United States Patent [19]

van Gerven

[11] 3,971,383
[45] July 27, 1976

[54] CRYOGENIC SURGICAL INSTRUMENT

[75] Inventor: Johannes T. M. van Gerven, Tubingen, Germany

[73] Assignee: Erbe Elektromedizin KG, Tubingen, Germany

[22] Filed: Apr. 29, 1975

[21] Appl. No.: 572,872

[30] Foreign Application Priority Data
May 7, 1974 Germany............................ 2422103

[52] U.S. Cl................................ 128/303.1; 62/293
[51] Int. Cl.²......................................... A61B 17/36
[58] Field of Search................ 128/303.1, 400, 401; 62/293

[56] References Cited
UNITED STATES PATENTS

| | | | |
|---|---|---|---|
| 3,266,492 | 8/1966 | Steinberg......................... | 128/303.1 |
| 3,298,371 | 1/1967 | Lee................................... | 62/293 X |
| 3,333,587 | 8/1967 | Johnston.......................... | 128/303.1 |
| 3,398,738 | 8/1968 | Lamb et al....................... | 128/303.1 |
| 3,507,283 | 4/1970 | Thomas, Jr....................... | 128/303.1 |
| 3,823,718 | 7/1974 | Tromovitch...................... | 128/303.1 |
| 3,907,339 | 9/1975 | Stumpf et al..................... | 128/303.1 |

*Primary Examiner*—John D. Yasko
*Attorney, Agent, or Firm*—Flynn and Frishauf

[57] ABSTRACT

To insulate the supply lines to an operating tip of a cryogenic surgical instrument, a coaxial assembly of tubes is provided, the inner one being connected to a supply of cryogenic liquid, such as liquid nitrogen; the space between the outer wall of the inner tube and the next tube forming a return line for evaporated cryogenic liquid which is vented to the atmosphere; and the space between the outermost one of the coaxial tubes and the intermediate tube containing a gas such as normal butane, introduced at atmospheric pressure and which has high heat-insulating properties, and which solidifies, or sublimates, to avoid a vacuum and make possible construction of the supply lines as plastic, preferably polyamide tubes, retaining flexibility in use.

10 Claims, 4 Drawing Figures

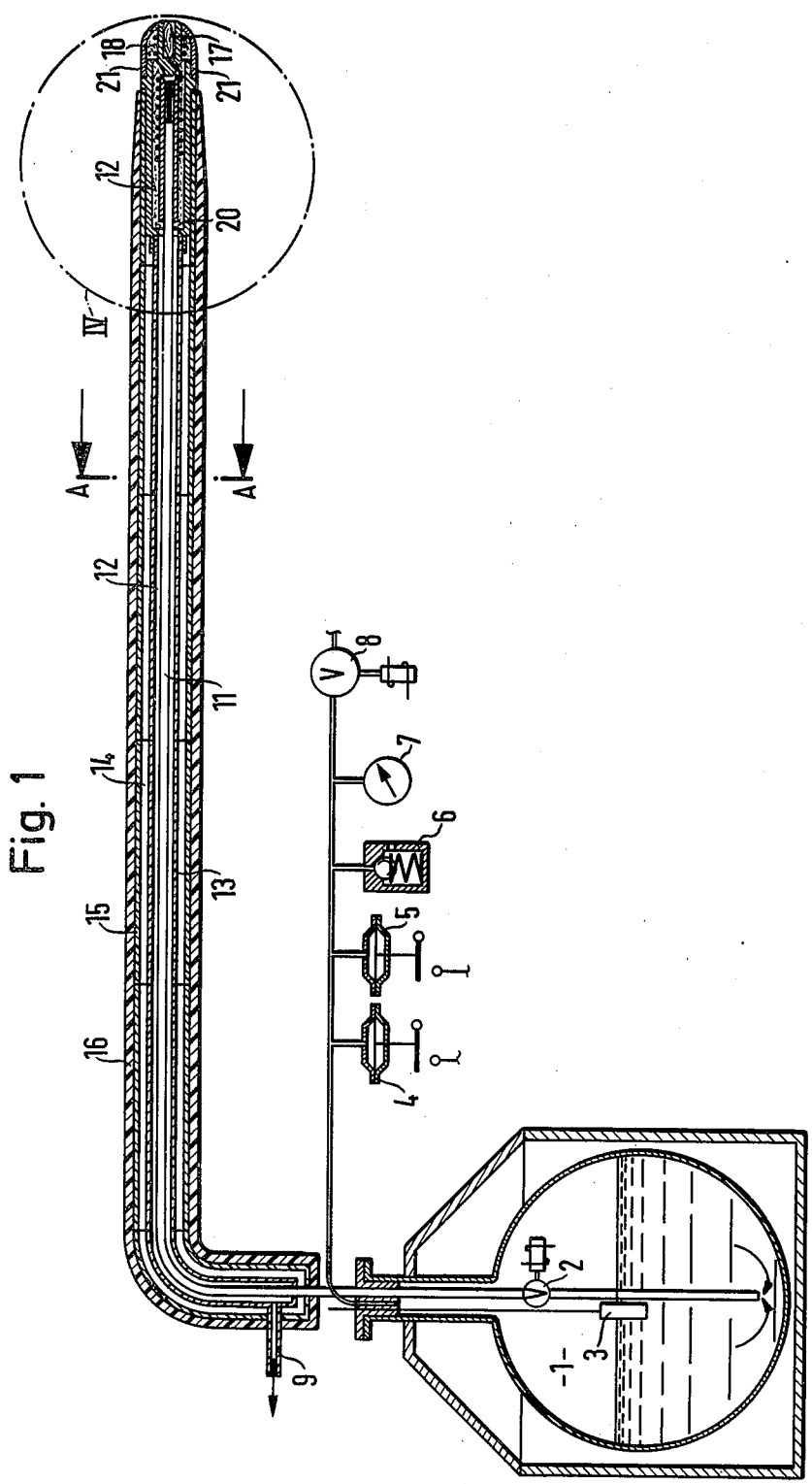

CRYOGENIC SURGICAL INSTRUMENT

The present invention relates to a cryogenic surgical instrument, and more particularly to a surgical instrument in which super-cooled, cryogenic fluid is conducted to a thermally conductive tip.

Cryogenic surgical instruments have been used in surgery with good results. To maintain the instrument at the proper temperature level, a chamber between an inner and an outer tube is evacuated to provide for thermal insulation (see German Pat. No. 1,243,822). It is difficult to manufacture probes or instruments of this kind in this manner, and for reasons of production and manufacturing simplicity it would be desirable to provide an instrument in which insulation by a vacuum chamber can be eliminated. Insulation of equal insulating quality, however, has not heretofore been found possible, although a heating arrangement in a layer of thermally insulating material has been contemplated.

It is an object of the present invention to provide a cryogenic surgical instrument which does not require insulation chambers subject to a high vacuum either in the instrument, or at the attached connecting lines to the instrument. Additionally, the connecting lines should be capable of being made only of plastic, or other highly flexible material, thus avoiding previously used metal tubing.

SUBJECT MATTER OF THE PRESENT INVENTION

Briefly, the instrument comprises coaxial tubes, in which the inner tube, preferably, is the supply line for cryogenic liquid and the outer, surrounding line is the return line, the outer surrounding line, in turn, being surrounded by a chamber, formed by an outermost tube, to provide heat insulation. In accordance with the invention, the chamber between the outer, return tube and the outermost tube contains a filler of normal butane. The chamber may, in accordance with a feature of the invention, additionally contain insulating ceramic powder such as Perlit (trademark) powder. To provide for additional insulation, the outside of the outermost tube can be additionally insulated by foam material.

The invention will be described by way of example with reference to the accompanying drawings, wherein:

FIG. 1 is a general, schematic longitudinal sectional view through a surgical cryogenic instrument, connected to a surgical cryogenic system;

Figure 3:
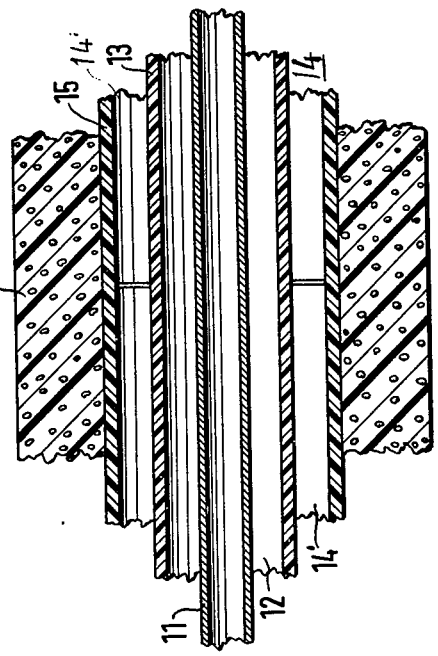
FIG. 3 is a highly enlarged sectional view of the instrument in the region of the section of FIG. 2.

An insulated vessel 1 (FIG. 1) is at least partly filled with liquid nitrogen. A supply line 11 for the surgical instrument extends into the liquid nitrogen. The other end of supply line 11 is connected to the thermally conductive tip of the instrument. The vessel 1 can be pressurized by means of a heater 3 to a pressure of about 3 atm. When this, or another similar preset pressure is reached, a pressure switch 4 is operated which interrupts the heating current to the heater 3. Switch 4 is connected to a tube which connects with the interior of the vessel 1. This pressure communicating tube is connected to a further pressure switch 5 which is connected to open a safety valve 8 when the pressure rises to a higher threshold level, for example to about 4 atm. An additional mechanical safety valve 6 is connected which has a still higher pressure threshold level, for example 4.5 atm.

A control valve 2 is connected in line 11; when control valve 2 is opened, liquid nitrogen is supplied to the cooling tip 21 (FIG. 4) where the liquid nitrogen vaporizes. The connecting line 11 is surrounded by an outer line 12, leaving a space therebetween, however; line 12 is formed by a plastic tube or pipe 13. In accordance with a feature of the invention, tube 13 comprises a polyamide tube. The space or chamber 12 formed between the tube 13 and the wall of tube 11 is used to conduct the evaporated nitrogen back and out from the tip of the cryogenic instrument; a vent opening 9 leads to the atmosphere to vent the evaporated nitrogen.

Figure 2:
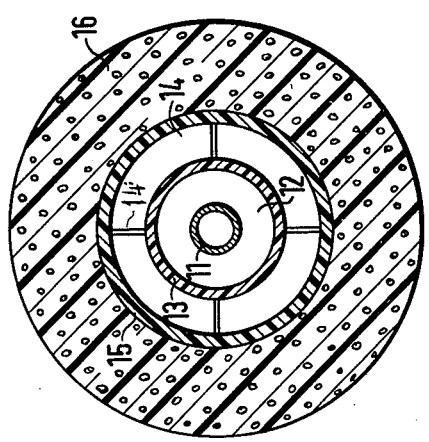
FIG. 2 is a transverse section taken along line A—A of FIG. 1.

The handle for the instrument and the connecting lines are best seen in FIGS. 2 and 3. The connecting line 11 is surrounded, with space forming the chamber 12, by the polyamide tube 13, the polyamide tube 13 defining an elongated tubular chamber between the outer wall of the connecting line 11 and the inner wall of the tube 13. The polyamide tube 13, in turn, is surrounded by an outermost polyamide tube 15 which is spaced from tube 13 to define an elongated tubular space 14. Tubular space 14, to provide insulation, is filled with a gas comprising normal butane. The outermost polyamide tube 15 is preferably coated or covered throughout its entire length with an insulating material 16. Material 16 is a thermoplastic foam material having closed cells, preferably, for example, using the plastic material "Armaflex" (trademark). The two polyamide tubes 13, 15 are maintained spaced from each other by spacers 14' made, for example of thin corrosion-resistant steel.

Figure 4:
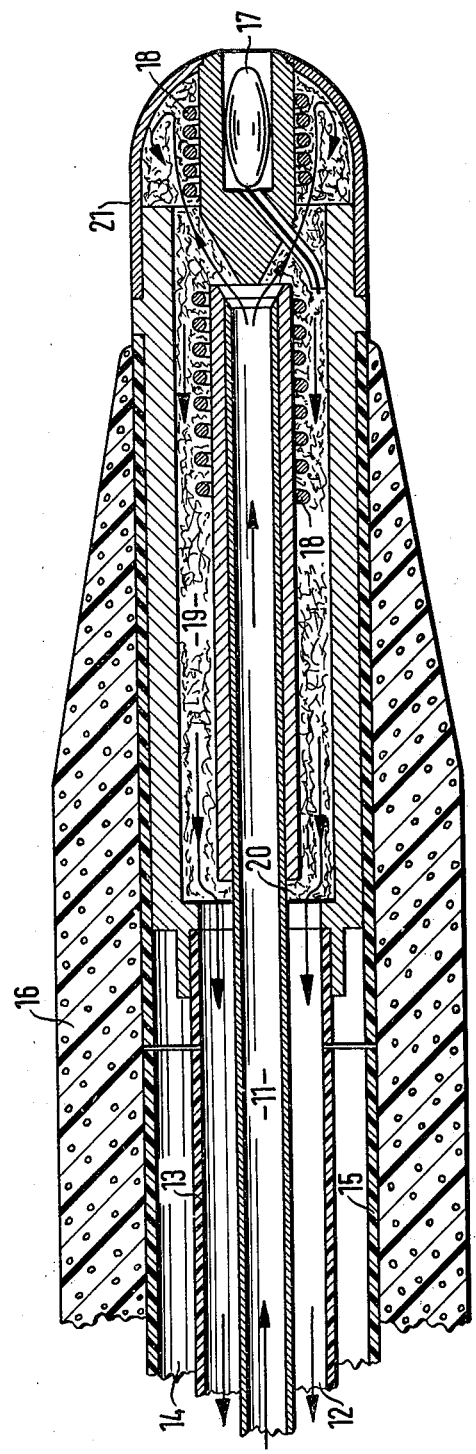
FIG. 4 is a longitudinal sectional view, to a greatly enlarged scale, of the region generally indicated by the chain-dotted circle IV of FIG. 1.

The operating end of the surgical instrument is best seen in FIG. 4. This end is so constructed that it can be introduced, for example, through the skull into the brain of a patient. The operating tip is not covered by the insulating coating or cover 16. The outermost polyamide tube 15 terminates on a cooling tip 21, made of a metal which is highly heat-conductive. The cooling or heat-conductive tip 21 has a temperature sensor 17 included therein. Temperature sensor 17, which may be an electrical resistance element, is electrically connected by wires (not shown in detail) which are connected to control the valve 2 in FIG. 1, in order to permit control of the temperature of the cooling tip 21. The cooling tip 21 further includes a heater winding 18. The power dissipation of the heater 18 is preferably so selected that the operating temperature of the tip can be raised to a temperature of about +30° C in less than one minute after having been cooled, so that the tip can be readily removed from contact with the patient.

Operation: Upon opening of control valve 2, liquid nitrogen is conducted into the hollow interior section of the cooling tip 21 (FIG. 4). The nitrogen so conducted into the cooling tip there evaporates, and is conducted back through the chamber 12 defined by polyamide tube 13, to be then vented through vent opening 9 into the atmosphere. The temperature of the nitrogen which evaporates is still very low; this cools polyamide tube 13 to such an extent that the butane at the outer wall of polyamide tube 13, that is, in chamber 14, will sublimate. The interior of the tip end 21 is hollow, the space thereof being filled with a fine metal wool 19, for example silver wire wool, or copper wool.

The probe or instrument is pre-cooled before an operation is carried out, until the crystalline sublimate layer at the outer wall of tube 13 is so thick that sufficient heat insulation is obtained. Thirty to 40 seconds are usually all that is needed to so pre-cool an instrument as illustrated. The temperature of the cooling tip 21 will then drop to about −180° C; the temperature at the surface of the outermost polyamide tube 15 will not drop below about +16° C even upon further operation of the instrument. The wire filling 19, which may be silver or copper wire, also functions as a barrier for return of liquid nitrogen; additionally, baffles can be used, or the interior of the tip 21 so shaped that return of liquid nitrogen is inhibited.

The insulating effect is improved with respect to vacuum insulation since the heat conductivity of plastics is comparatively low. Due to sublimation of the gas in chamber 14, upon operation, additional decrease in heat conductivity is obtained. Due to the sublimation, the chamber 14, normally filled with normal butane, will be subjected to a certain under-pressure, or vacuum; this under-pressure, below atmospheric, is not so great, however, as to place severe requirements on the mechanical strength of the polyamide tube, and much less than the mechanical strength requirements if a high vacuum, to provide thermal insulation, were to be used in the chamber 14. Filling the insulating chamber 14 with normal butane during manufacture does not introduce substantial manufacturing difficulties. It is only necessary to evacuate the space 14 to about $10^{-2}$ Torr, so that essentially all contaminants or other materials, such as water vapors, are removed. To additionally drive out any contaminants, heating to 180° C, for a period of about 4 days may be desirable. Thereafter, space 14 is filled with normal butane under atmospheric pressure. Due to the careful cleaning of the walls of the polyamide tubes defining the chamber 14, a molecular layer of normal butane will form thereon which, apparently, accelerates sublimation. In operation, cooling to about 0° C is achieved in about eight seconds. Condensation formation from normal butane could be observed during one second already, after which time the temperature will then drop to below −5° C, and sublimation will occur.

The instrument of the present invention has an additional advantage: Only a comparatively low over-pressure arises at the instrument tip, since the return line or chamber 12 is vented to the atmosphere at vent 9. The operating pressure, thus, is low; the underpressure, or degree of vacuum, in the insulating chamber likewise is low (in contrast to an insulating vacuum), and thus greater safety in use of the instrument is ensured for the patient during operations. The heating coil 18 can be so located in the instrument that the instrument can be quickly heated, and thus removed from the patient since, upon heating, and due to the vent connection 9 of the return line 12, no pressure can build up upon heating the tip 21. Still, in order to provide for complete vaporization of any liquid nitrogen supplied to the instrument when in use, a liquid barrier is located at the junction 20 at the exit of vaporized material from the interior of the cooling tip 21 to the return chamber 12; this liquid barrier may be a ring in form of a baffle, or merely a constriction to form a very small exit opening to pass only evaporated nitrogen. Such a construction is shown in FIG. 4 at 20.

The outer foam insulation covering 16 (FIGS. 2, 3) extends along the length of the connecting line until almost to the tip of the instrument itself. This insulating tubing 16 is desirable since the instrument tip is rapidly cooled upon evaporation of the liquid nitrogen; upon initiation of the cooling, however, the sublimate layer in the region of the connecting line is still too thin; providing the additional insulating coating 16 accelerates formation of the sublimation layer. The sublimation layer will thus form more rapidly. Additional acceleration of formation of the sublimate layer is possible by providing a heat-insulating ceramic powder in the space 13. A suitable powder is Perlite (trademark), which provides good heat insulation, since only point-spaced heat bridges or connecting junctions will arise between the pellets or grains of the powder; the heat conductivity of the powder is, therefore, very low.

The filling of n-butane provides for sufficient heat insulation; upon supplying liquid cryogenic fluid, that is, for example liquid nitrogen, a condensation layer of crystalline n-butane will occur in the chamber 14, that is, on the outer wall of the tube 13 which defines chamber 12 through which the evaporated cryogenic fluid is conducted back and vented to the atmosphere. Thus, sufficient heat insulation is ensured upon use of the instrument. A certain under-pressure, or vacuum will occur in the space 14 which, however, is so small in comparison to the vacuum which would be required for vacuum-thermal insulation that the previously metallic corrugated tubes can be eliminated and, instead, connecting lines of polyamide or similar plastics may be used which, of course, are much more flexible than metal lines. Use of such plastic tubes as outer connections for the instrument, connected to the tip of the instrument also ensures better limitation and definition of the zone to be cooled since only small heat supply from the biological substance of the patient is necessary in order to retain the surface of the outermost polyamide tube at a sufficient temperature to prevent freezing of tissue in contact therewith, or to prevent otherwise undesirable cooling. The supercooled zone is thus accurately defined and limited, since the heat conductivity of the plastic material is much less than the heat conductivity of metallic supply tubes which, previously, were connected to known instruments of this type at the cooling tip itself.

The present invention has been described in connection with a filler for chamber 14 of normal butane. The main, important feature of the invention is, however, that rather than using a vacuum as an insulation, a gas is used which has certain physical characteristics — namely that it has good heat-insulating properties and, particularly when solidifying, provides a mono crystal of open structure of high heat-insulating properties, the solidification temperature being within the range which occurs at the outer wall surface of the polyamide tube 13, thereby maintaining the various polyamide tubes in a state of good flexibility. Other than n-butane, hydrocarbons such as $C_4H_8$ 1-Butene or $C_4H_6$ 1.3-Butadiene are suitable. Other gases than hydrocarbons, or substituted hydrocarbons, and having the physical characteristics above enumerated may also be used, for example: $F_2Cl_2Si$ DichorodiFluorosilane, but not recommended n-butane is preferred due to its safety in use and easy availability, although other gases which are equally safe in case of leakage, and having the requisite physical characteristics may also be employed in surgical procedures.

Using polyamide for the lines 11, 13 and 15 permits the use of readily available materials, which are easily connected to the tip 21. Other materials may also be used for the tubes, for example: TEFLON (PTFE).

I claim:
1. Cryogenic surgical instrument to supercool limited areas of biological tissue having
   a hollow tip (21) of thermally conductive material, a supply vessel (1) of supercooled cryogenic liquid,
   a supply line (11) connected to said supply vessel (1) and to the hollow interior of the tip (21),
   a return line coaxial with said supply line and surrounding the same, said return line comprising two coaxial tubes (13, 15) spaced from each other and defining a heat-insulating space (14) therebetween, the inner one of the coaxial tubes (13) being spaced from the supply line (11) to define a return space (12) for evaporated cryogenic liquid,
   and a filler material comprising n-butane in said insulating space (14).
2. Instrument according to claim 1, further comprising additional filler material comprising insulating ceramic powder located in said insulating space (14).
3. Instrument according to claim 1, wherein at least one of said coaxial tubes (13, 15) comprises a polyamide tube.
4. Instrument according to claim 1, further comprising spacers (14') spacing said inner and outer coaxial tubes (13, 15) from each other.
5. Instrument according to claim 1, wherein the outermost one (15) of said coaxial tubes (13, 15) is directly connected to said tip (21).
6. Instrument according to claim 1, further comprising an insulating layer or cover (16) comprising foam material with closed cells surrounding the outer one of said coaxial tubes, at least in part.
7. Instrument according to claim 1, further comprising a filling (19) in the hollow interior of the cooling tip, said filling comprising a material including at least one of: silver wool; copper wool.
8. Instrument according to claim 1, further comprising a heating winding (18) located in the hollow interior of the cooling tip (21).
9. Instrument according to claim 1, further comprising a vent opening (9) communicating with the return space (12) between the supply line (11) and the inner one of said coaxial tubes (13), said vent opening being in communication with ambient atmosphere.
10. Instrument according to claim 1, further comprising a liquid barrier (20) in the interior of the cooling tip (21) in the path of the return space (12) to prevent escape of cryogenic substance in liquid phase from the interior of the cooling tip.

* * * * *